US006149577A

United States Patent [19]
Bouldin et al.

[11] Patent Number: 6,149,577
[45] Date of Patent: *Nov. 21, 2000

[54] APPARATUS AND METHOD FOR CREATING A SUBSTANTIALLY CONTAINED, FINITE MAGNETIC FIELD USEFUL FOR RELIEVING THE SYMPTOMS PAIN AND DISCOMFORT ASSOCIATED WITH DEGENERATIVE DISEASES AND DISORDERS IN MAMMALS

[75] Inventors: Floyd E. Bouldin, Murfreesboro; C. Douglas Williams, Signal Mountain; Rick R. Wascher, Rock Island, all of Tenn.

[73] Assignee: EMF Therapeutics, Inc., Chattanooga, Tenn.

[*] Notice: This patent is subject to a terminal disclaimer.

[21] Appl. No.: 09/271,884

[22] Filed: Mar. 18, 1999

[51] Int. Cl.[7] .............................. A61B 17/52; A61N 1/00
[52] U.S. Cl. .................................. 600/13; 600/9; 600/14
[58] Field of Search ............................................ 600/9–15

[56] References Cited

U.S. PATENT DOCUMENTS

| Re. 32,947 | 6/1989 | Dormer et al. . |
|---|---|---|
| 96,044 | 10/1869 | Smith . |
| 703,989 | 7/1902 | Burry . |
| 770,433 | 9/1904 | Kinraide . |

(List continued on next page.)

FOREIGN PATENT DOCUMENTS

| 0 048 451 | 3/1982 | European Pat. Off. . |
|---|---|---|
| 0 181 053 | 5/1986 | European Pat. Off. . |
| 0 371 504 | 6/1990 | European Pat. Off. . |

OTHER PUBLICATIONS

Guterl, Fred; "Beauty and Magnets"; Discover Magazine, Mar. 1997 pp. 38–43.

O'Brien, Jim; "Revolutionary New Magnetic Therapy Kos Arthritis Pain", Your Health Magazine, Apr. 6, 1993, pp. 17–18.

Chemical Abstracts, vol. 128, No. 14 Apr. 6, 1998, Ikeda, Shigeki et al.; "Enhancement of the effect of an angiogenesis inhibitor on murine tumors by hyperthermia".

Chemical Abstracts, vol. 124, No. 3, Jan. 15, 1996, Robins, H. Ian et al.; "Cytokine induction by 41.8 degree C whole body hyperthermia".

Bone, vol. 19, No. 1 Supplement, Jul. 1996, pp. 39S–57S, by H. Winet, "The Role of Microvasculature in Normal and Perturbed Bone Healing as Revealed by Intravital Microscopy".

Proceeding Abstract of the $4^{th}$ EBEA Congress, Zagreb, Croatia, Nov. 19–21, 1998; G. Sersa et al., "Tumour Blood Flow Changes Induced by Application of Electric Pulses".

Abstract and Article: Journal of Cellular Physiology 134:37–45 (1988); Yen–Patton, et al., "Endothelial Cell Response to Pulsed Electromagnetic Fields: Stimulation of Growth Rate and Angiogenesis in Vitro".

*Primary Examiner*—Cary O'Connor
*Assistant Examiner*—Ryan Carter
*Attorney, Agent, or Firm*—Rick R. Wascher

[57] ABSTRACT

A method and apparatus for relieving pain associated with degenerative diseases and disorders in biological subjects such as mammals. The method employs the use of an apparatus which is capable of producing a magnetic field of a particular nature which has been proven in human tests to dramatically reduce pain. An embodiment of the apparatus includes a frame, a plurality of magnets capable of producing a magnetic field wherein each of the plurality of magnets has a north pole and a south pole and a longitudinal axis passing therethrough and are partially held in place by the frame. Another embodiment incorporates a coil of electrically conducting material is wrapped about a frame, and/or the plurality of magnets in an orthogonal relationship to the longitudinal axis of each of the plurality of magnets. A source of electrical energy supplies an electrical current to the coil enabling a magnetic field to be produced therefrom. A switch is provided to enable the electrical current to flow in a first direction and optionally in a second direction opposite to the first direction. A rectifier is provided to alter the inherent supply voltage (e.g., 60 hertz) to a 120 hertz half sine or corresponding DC square wave form.

20 Claims, 7 Drawing Sheets

U.S. PATENT DOCUMENTS

| | | |
|---|---|---|
| 781,448 | 1/1905 | McIntyre . |
| 2,102,790 | 12/1937 | Drollinger . |
| 3,570,476 | 3/1971 | Gregg . |
| 3,890,953 | 6/1975 | Kraus et al. . |
| 3,915,151 | 10/1975 | Kraus . |
| 4,066,065 | 1/1978 | Kraus . |
| 4,134,395 | 1/1979 | Davis . |
| 4,233,965 | 11/1980 | Fairbanks . |
| 4,303,636 | 12/1981 | Gordon . |
| 4,402,309 | 9/1983 | Harrison . |
| 4,622,952 | 11/1986 | Gordon . |
| 4,626,792 | 12/1986 | Liboff et al. . |
| 4,641,633 | 2/1987 | Delgado . |
| 4,674,482 | 6/1987 | Waltonen et al. . |
| 4,765,310 | 8/1988 | Deagle et al. . |
| 4,818,697 | 4/1989 | Liboff et al. . |
| 4,838,850 | 6/1989 | Rosengart . |
| 4,889,526 | 12/1989 | Rauscher et al. . |
| 4,932,951 | 6/1990 | Liboff et al. . |
| 4,940,453 | 7/1990 | Cadwell . |
| 4,993,413 | 2/1991 | McLeod et al. . |
| 4,994,015 | 2/1991 | Cadwell . |
| 5,000,178 | 3/1991 | Griffith . |
| 5,010,897 | 4/1991 | Leveen . |
| 5,014,699 | 5/1991 | Pollack et al. . |
| 5,030,196 | 7/1991 | Inoue . |
| 5,045,050 | 9/1991 | Liboff et al. . |
| 5,047,005 | 9/1991 | Cadwell . |
| 5,059,298 | 10/1991 | Liboff et al. . |
| 5,061,234 | 10/1991 | Chaney . |
| 5,066,272 | 11/1991 | Eaton et al. . |
| 5,067,940 | 11/1991 | Liboff et al. . |
| 5,077,934 | 1/1992 | Liboff et al. . |
| 5,078,674 | 1/1992 | Cadwell . |
| 5,084,003 | 1/1992 | Susic . |
| 5,085,626 | 2/1992 | Frey . |
| 5,085,627 | 2/1992 | Federov et al. . |
| 5,087,336 | 2/1992 | Liboff et al. . |
| 5,088,976 | 2/1992 | Liboff et al. . |
| 5,090,423 | 2/1992 | Matsuda et al. . |
| 5,100,373 | 3/1992 | Liboff et al. . |
| 5,106,361 | 4/1992 | Liboff et al. . |
| 5,116,304 | 5/1992 | Cadwell . |
| 5,123,898 | 6/1992 | Liboff et al. . |
| 5,131,904 | 7/1992 | Markoll .................................... 600/14 |
| 5,143,588 | 9/1992 | Liboff et al. . |
| 5,156,587 | 10/1992 | Montone . |
| 5,160,591 | 11/1992 | Liboff et al. . |
| 5,183,456 | 2/1993 | Liboff et al. . |
| 5,195,940 | 3/1993 | Baylink . |
| 5,211,622 | 5/1993 | Liboff et al. . |
| 5,215,633 | 6/1993 | Liboff et al. . |
| 5,215,642 | 6/1993 | Liboff et al. . |
| 5,224,922 | 7/1993 | Kurtz . |
| 5,267,939 | 12/1993 | Liboff et al. . |
| 5,269,745 | 12/1993 | Liboff et al. . |
| 5,269,746 | 12/1993 | Jacobson . |
| 5,290,409 | 3/1994 | Liboff et al. . |
| 5,312,321 | 5/1994 | Holcomb . |
| 5,312,534 | 5/1994 | Liboff et al. . |
| 5,314,400 | 5/1994 | Tsyb et al. . |
| 5,318,561 | 6/1994 | McLeod et al. . |
| 5,330,410 | 7/1994 | Baylink . |
| 5,344,384 | 9/1994 | Ostrow et al. . |
| 5,357,958 | 10/1994 | Kaufman . |
| 5,366,435 | 11/1994 | Jacobson . |
| 5,368,544 | 11/1994 | Tran et al. . |
| 5,387,176 | 2/1995 | Markoll . |
| 5,415,617 | 5/1995 | Kraus . |
| 5,437,600 | 8/1995 | Liboff et al. . |
| 5,441,495 | 8/1995 | Liboff et al. . |
| 5,453,073 | 9/1995 | Markoll ................................ 600/15 X |
| 5,458,558 | 10/1995 | Liboff et al. . |
| 5,476,438 | 12/1995 | Edrich et al. . |
| 5,518,495 | 5/1996 | Kolt . |
| 5,518,496 | 5/1996 | McLeod et al. . |
| 5,525,949 | 6/1996 | Hanley et al. . |
| 5,541,563 | 7/1996 | Leupold . |
| 5,658,234 | 8/1997 | Dunlavy . |
| 5,665,049 | 9/1997 | Markoll . |
| 5,669,868 | 9/1997 | Markoll . |
| 5,842,966 | 12/1998 | Markoll ................................... 600/14 |
| 5,880,661 | 3/1999 | Davidson et al. . |
| 6,007,476 | 12/1999 | Wascher et al. ...................... 600/13 X |

APPARATUS AND METHOD FOR CREATING A SUBSTANTIALLY CONTAINED, FINITE MAGNETIC FIELD USEFUL FOR RELIEVING THE SYMPTOMS PAIN AND DISCOMFORT ASSOCIATED WITH DEGENERATIVE DISEASES AND DISORDERS IN MAMMALS

BACKGROUND OF THE INVENTION

Field of the Invention

The present inventive discovery is directed to the use of a device capable of producing a finite or substantially contained magnetic field or flux field. The inventive device and related discovery uses a magnetic flux field which has been determined to be capable of relieving pain associated with degenerative diseases and disorders in mammals such as humans.

Pain is considered an unpleasant sensory and emotional experience associated with actual or potential tissue damage or described in terms of such damage. This definition, formulated in 1980 by the International Association for the Study of Pain, emphasizes the psychological contribution to the experience of pain. (The same group has also used the term nociception—from the word noxious—for the experiencing of a stimulus that is tissue damaging.) Thus, the definition is primarily applicable to humans. Pain is also the single most common complaint for which people visit doctors.

Animals exhibit behavior that can be labeled pain, and such behaviors have been studied intensively in research on the mechanisms of pain and in trials of potential pain-relieving drugs; but whether animals have the strong psychological component to pain that humans do is doubtful.

Acute pain starts with the stimulation of one or more of the many special sense receptors, called nociceptors, in the skin or internal organs. These receptors receive information about intense heat, extreme pressure, sharp pricks or cuts, or other events that can cause body damage. Two types of nerve fibers carry this information from the nociceptors to the spinal cord: A-delta fibers, which transmit information quickly and appear to be responsible for the acute sense of pain; and C-type fibers, which transmit impulses more slowly and may cause the nagging sense of pain.

At the spinal cord, messages from nociceptors may be modulated by other spinal nerves that enhance or, more frequently, diminish the intensity of the pain stimulus. The impulse then travels to several parts of the brain. Some brain areas determine where the pain is and what is causing it, while other areas integrate the sensory information with the total state of the organism and produce the emotional sensation called pain. These same brain centers can activate long nerve fibers that descend to the place in the spinal cord where the pain signal originates and decrease the signal.

In the mid-1970s, researchers showed that many fibers that inhibit pain messages in the spinal cord release a neurotransmitter called enkephalin. Some areas of the brain that process pain messages secrete a related chemical called endorphin. Although the exact roles of these two substances in pain perception is not yet clear, scientists hope that studies of these chemicals may eventually give rise to better modes of pain treatment.

The complex nature of pain is illustrated by anecdotes about soldiers who are severely wounded and do not complain of pain, or of athletes who are injured but do not experience pain until the contest is over. In some cultures, an operation called trepanning is performed on the skull without anesthetic. On the other hand, scientists have recently shown that the expectation of pain can actually intensify the experience, perhaps by inducing anxiety. The emotional component of pain is also illustrated by words frequently used to describe it, such as "vicious," "nauseating," and "nagging."

Acute pain—such as that produced by physical trauma or burns or following surgery—is most often treated with analgesic drugs, which can range from aspirin to morphine. In the terminal stages of cancer, combinations of painkilling drugs may be used, including psychotropic medication such as a tranquilizer or an antidepressant. In some patients who have had surgery, pain is effectively relieved by a nerve block: the injection of an anesthetic into the regional nerve center through which the nerves from the surgery site pass. With certain types of back pain, surgery can correct the problem causing it.

Beginning about 1965, physicians came to appreciate the uniqueness of the condition called chronic pain. In this syndrome, patients may complain of pain for years, without having any apparent organic injury as cause. Researchers suggest that chronic pain is a behavior state, initiated by a real injury, in which the pain has lasted so long that it has itself become the disease. Of the many millions of Americans who suffer from chronic pain, one-third have back pain and another third arthritis. Many of these patients are dependent on strong painkilling medicines, and they usually have fallen into a cycle of pain, depression, and inactivity.

A number of special clinics have been formed to treat people who suffer from chronic pain. Such clinics emphasize reduction of drug dosages, along with exercise, activity therapy, and relaxation techniques such as hypnosis and biofeedback. Some include psychological counseling, and many attempt to change learned pain behaviors by enlisting the patient's family. In other cases, patients are helped by an electronic device, called a transcutaneous electronic nerve stimulator, that can be activated to send an electronic current up the spinal cord. How this device works is not known, but it may stimulate the brain to send pain-inhibiting impulses down the spine.

Temporomandibular Disorder (TMD), sometimes referred to as myofacial pain dysfunction or temporomandibular joint (TMJ) syndrome, disorder involving the muscles of the jaw used for chewing (masticatory muscles) and/or the temporomandibular joint, which connects the lower jaw to the skull.

The chief symptom of TMD is pain, typically in the jaw muscles, the region in front of the ear, and the temporomandibular joint. Limitations in using the jaw comfortably and joint sounds (clicking, popping, or grating noises) when the jaw is being used are also commonly present. However, many people (approximately 25 percent) normally have such joint sounds in the absence of pain. Pain can spread to the muscles of the shoulders and neck. Much more rarely, TMD can cause disturbances of vision and balance.

Although TMD is a fairly common chronic pain disorder, its causes are only poorly understood; they may include trauma to the face, grinding of the teeth (bruxism), and arthritis. "Bad bite," or malocclusion of the teeth, is no longer considered a cause of TMD. Stress and other emotional factors appear to play an important role in TMD but are probably more a reaction to the painful condition than a cause of it.

Conventional treatment methods emphasizes a combination of conservative, reversible therapies, such as muscle relaxation exercises, analgesics, and sometimes removable bite plate appliances—plastic devices, usually worn during sleep, that cover the chewing surfaces of the upper teeth and discourage teeth grinding. Surgery of the temporomandibular joint is necessary only in a few severe cases.

SUMMARY OF THE INVENTION

Magnetism is a property of charge in motion and is related to electrical theory. Each individual atom of magnetic substance is, in effect, a tiny magnet with a north pole and a south pole. Magnetic properties of materials may be classified as diamagnetic, paramagnetic, and ferromagnetic. Their classification relates to the manner in which materials react in a magnetic field. For example, certain solids such as iron are strongly attracted to magnets. Such materials are called ferromagnetic.

Magnetism is also related to current flowing in a conductor. A magnetic field surrounds a current carrying conductor according to the well known "right hand rule". Conversely, it is also known that a magnetic field of flux can induce current flow in circuits.

An embodiment of the present invention is directed to a device for establishing or otherwise creating a substantially contained finite, preferably planar, magnetic field comprised of magnetic and/or electro-magnetic components. The preferred embodiments of the present invention are devices found capable of generating a magnetic field to relieve the symptoms associated with degenerative diseases and disorders, including, pain, swelling, stiffness, etc.

The devices may be configured to include permanent magnets, a coil or plurality of coils of conductor to create magnetism, or both (hereinafter "three phase" capability). A magnetic field produced by a permanent magnet source can be said to constitute a first phase. A magnetic field produced solely by a current carrying coil or plurality of coils of wire can be said to constitute a second phase. A magnetic field created from a current carrying wire in conjunction with the magnetic field associated with the permanent magnetic source can be said to constitute a third phase. The third phase can be further described as "additive" or "opposing". Additive means the direction of the field lines for the permanent magnetic field source and the current carrying coil source are similarly oriented in direction. Opposing refers to the situation where the aforementioned field lines are in opposing direction.

The embodiments of the apparatus of the present invention include: (1) permanent magnets, (2) a current carrying wire for producing a magnetic field around it where the lines of magnetic flux are clockwise or counterclockwise around the wire when viewed from a hypothetical common cross-sectional face, or (3) a combination of (1) and (2), so long as a substantially planar magnetic field is produced therefrom.

The embodiments of the present invention were found useful for relieving pain associated with degenerative diseases and disorders including TMJ pain by establishing a contained magnetic field and exposing the pain region to the field. One of the embodiments includes a plurality of permanent magnets oriented in a side by side axis parallel orientation such that the longitudinal axis and poles of a first magnet are placed adjacent to and parallel with the longitudinal axis of an adjacent or second magnet of similar but not necessarily identical configuration or properties.

Another of the embodiments includes a coil of conductor such as a length of wire with a voltage drop applied to its opposing ends. The planar or confined finite nature of the field is attributable, for the most part, to a frame onto which the coil(s) is/are wound or the permanent magnets attached. Thus, the coil is supported by a frame onto which it is wound and the frame may also hold permanent magnets.

Symptomatic relief (e.g., pain, swelling, etc.) through the use of the apparatus of the present invention is believed to be most prominent within the central passage way of the frame and preferably through coil(s), and/or the belt of permanent magnets, where the field can be said to be finite, and substantially planar in nature because it is bounded by the frame. Further studies, however, may also reveal that the magnetic field emanating from the front or rear face (i.e., the spaced apart sides of the frame) is also effective.

The preferred number of coil wire turns may vary but is believed to be optimal from between two hundred (200) and one thousand six hundred (1600) turns of insulated copper wire, because of the heat generated in the coil due to the inherent resistance of the wire to carry a current.

The preferred frame is shaped to form a circle, rectangle, square or other shape, such as the preferred ellipse having a central passageway or opening. An enclosed shape is believed highly preferred in order to establish the desired confined or finite field. Other means of establishing a contained, finite, preferably planar magnetic field, for example a magnetic field generator have a field emitting face or plate, are believed to be more difficult to create and thus less desirable than the frames and geometries of the present invention.

It is important to point out, the terms "finite" and "planar", as well as "contained" are used in a relative sense. That is, the magnetic filed established within the area bounded by the frame (i.e., the passageway) will have a magnetic field which may vary in flux density depending upon the location sampled, but remain confined, finite, and planar with respect to the physical boundary of the frame which defines the size and shape of the treatment passageway.

Within the coil assembly, or belt of magnets, is at least one optional thermal sensor of either the resistance or thermo-couple type. The sensor(s) measure and indicate the coil temperature at various points, and allow the operator of the device to monitor the potential decay of the permanent magnets, if any, which may be weakened by the generated heat of the device depending upon their composition.

The preferred power supply incorporates a transformer capable of delivering current within the preferred amperage range of 0–15 amps of current, the corresponding voltage for which would depend upon the number of turns of wire used to form the coil.

The voltage difference applied to the coil is passed through a voltage regulating device preferably in the nature of a full-wave rectifier set. By passing the output of the rectifier through a switch assembly the operator may regulate the applied current, and thus the generated field can be changed at will by the operator. The rectifier converts the applied alternating current to a direct current (DC) with a resulting ripple frequency of 120 pulses per second. The nature of the wave form is, therefore, best described as a modified one half sine wave formation, because the portion of the wave below the base line dividing the wave form is inverted upward above thereby resulting in the 120 pulses a second.

Of course, the 120 pulses a second presumes a 60 cycle supply voltage common in the United States, but may also be a 50 cycle supply voltage which is common in Europe thereby giving rise to 100 pulses per second frequency or other supply voltage that proves useful. In fact, it is believed by some that frequency modulation will enhance the beneficial results of the inventive method and apparatus.

With respect to the embodiment of the present invention which includes the optional permanent magnets, at least one magnet is removed from the plurality in order to create a gap in the elliptical string thereof. Physically leaving out magnets during the assembly process and replacing them with non-magnetic material or simply providing an air space insures the magnets themselves do not become current carrying conductors and destroy or unnecessarily affect their integrity during operation of the device.

A cover is attached to the frame to shield the coil. The cover, for example, may be a cooperating cover and frame sized to establish a passage between the coil and the cover to form at least one duct enabling gaseous flow into and out of the passage from a location outside of the passage.

The method of the present invention may be summarized in a variety of ways, one of which is the following: a method of relieving pain associated with degenerative diseases and disorders comprising the steps of: providing a DC magnetic field generating device having three phase magnetic field generating capability including a magnetic field component generated by a current carrying coil; energizing the current carrying coil enabling the DC magnetic field to be concentrated within a substantially planar area defined by a central passageway of a device frame; and placing a biological subject in the DC magnetic field and exposing the biological subject to said DC magnetic field.

The method has been found useful for relieving pain associated with degenerative diseases and disorders categorized within the pain group consisting of: myofacial pain, plantar fascitis, back, leg and neck pain. The preferred method also includes providing a combined DC magnetic field generating device with a plurality of turns of wire and a plurality of permanent magnets; applying an electrical voltage drop across the ends of the wire with the current being greater than 1 amp and less than 15 amps, but preferably between 5 amps and 10 amps.

The apparatus of the present invention may be summarized in a variety of ways, one of which is the following: an apparatus for relieving pain associated with degenerative diseases and disorders in humans, comprising means for producing a magnetic field, wherein the means includes a frame having a continuous sidewall and a central passageway extending therethrough, a coil made of electrically conducting material wrapped about the frame and the central passageway; and a source of DC electrical energy operably connected to the coil for supplying DC electrical current to the coil and establishing a DC magnetic field concentrated within a substantially planar area defined by the central passageway and bounded by the frame. A cover is attached to the frame to shield the coil.

An optional switch capable of regulating the direction of the current flow through the wire is also preferred, and the frame is substantially elliptical. Instead of a single coil, a plurality of coils may be used. The at least one coil has preferably between 200 and 800 turns of wire.

The apparatus may also be summarized as an apparatus for relieving pain associated with degenerative diseases and disorders in biological subjects comprising a means for producing a DC magnetic field concentrated within a substantially confined area, wherein the means includes: a frame having spaced apart sides and a central passageway extending therethrough; a coil made of electrically conducting material wrapped about the frame to overlie the central passageway; and a source of DC electrical energy operably connected to the coil for supplying DC electrical current to the coil to establish a DC magnetic field concentrated within a substantially planar area defined by the central passageway and bounded by the frame.

A plurality of optional magnets are positioned adjacent the coil and constrained from movement by the frame, wherein each of the plurality of magnets has a north pole and a south pole and a longitudinal axis passing therethrough, the plurality of magnets are positioned in a side by side axis parallel orientation and are partially held in place by the frame. In the preferred arrangement, the plurality of magnets are positioned to enable the like poles of a majority of the plurality of magnets to be adjacent one another.

The present invention also includes a means for producing a substantially planar, contained, magnetic field capable of relieving pain associated with degenerative diseases and disorders in humans, comprising: a frame having spaced apart sides, a central passageway formed through, and bounded by, each of the spaced apart sides of the frame to define a substantially planar area within the frame; a coil made of electrically conducting material wrapped about the frame and contained within the spaced apart sides; and a source of DC electrical energy operably connected to the coil for supplying DC electrical current to the coil to establish a DC magnetic field concentrated within the substantially planar area.

In addition, the present invention may also be summarized as follows: a device for relieving pain associated with degenerative diseases and disorders such as myofacial pain, plantar fascitis, back, leg and neck pain comprising: a frame having spaced apart side defining a central passageway and a substantially planar area thereof confined within the frame and bounded by an inside edges of each of the spaced apart sides; coil means including a source of DC electrical energy operably connected to at least one coil of electrically conducting wire enabling a DC electrical current to be applied to the wire for establishing a DC magnetic field concentrated within the substantially planar area defined by the central passageway and bounded by the frame.

All of the objects, features, and advantages of the present invention are believed to be within the scope of the present invention, even though they are not specifically set forth in this document.

DETAILED DESCRIPTION OF THE PREFERRED EMBODIMENT(S)

Figure 1A:
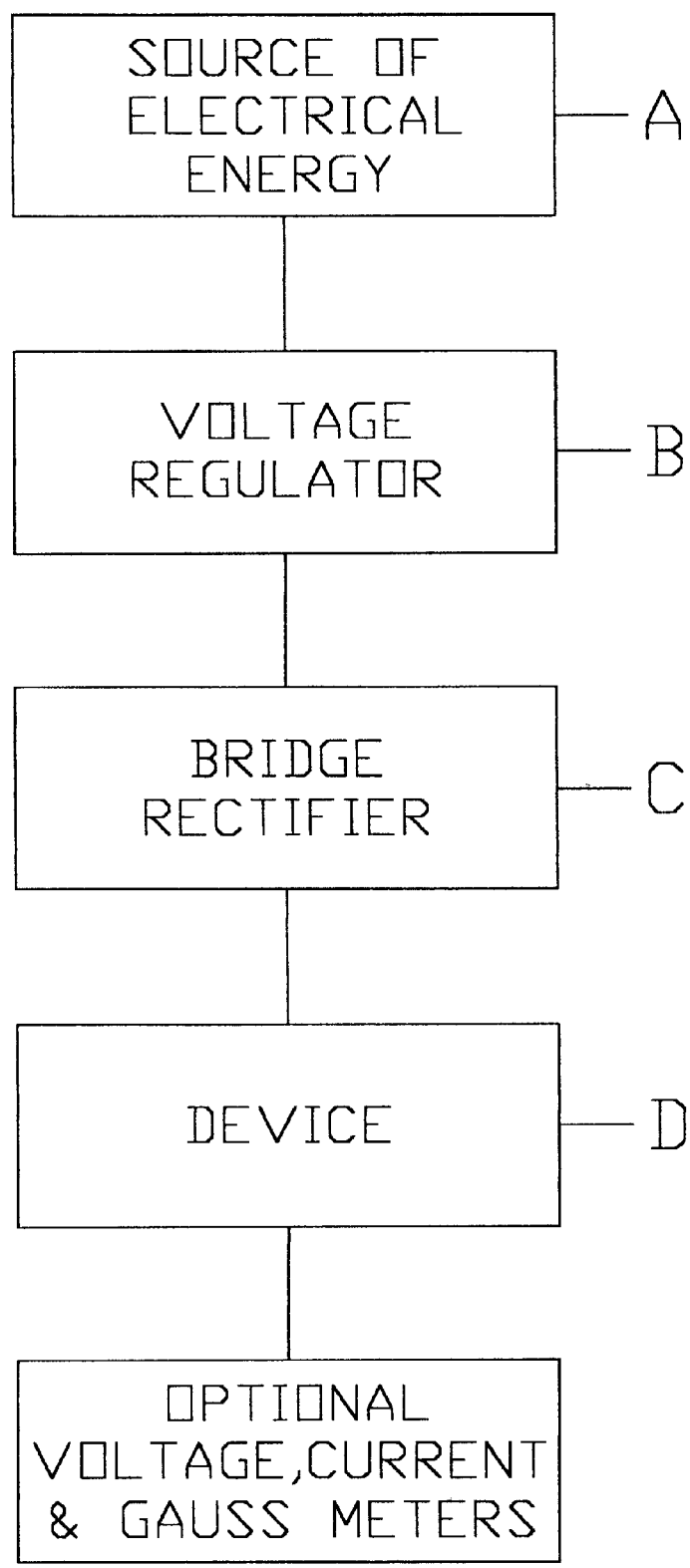
FIGS. 1A and 1B are schematic block diagrams of the electrical components of the present invention.
Figure 1B:
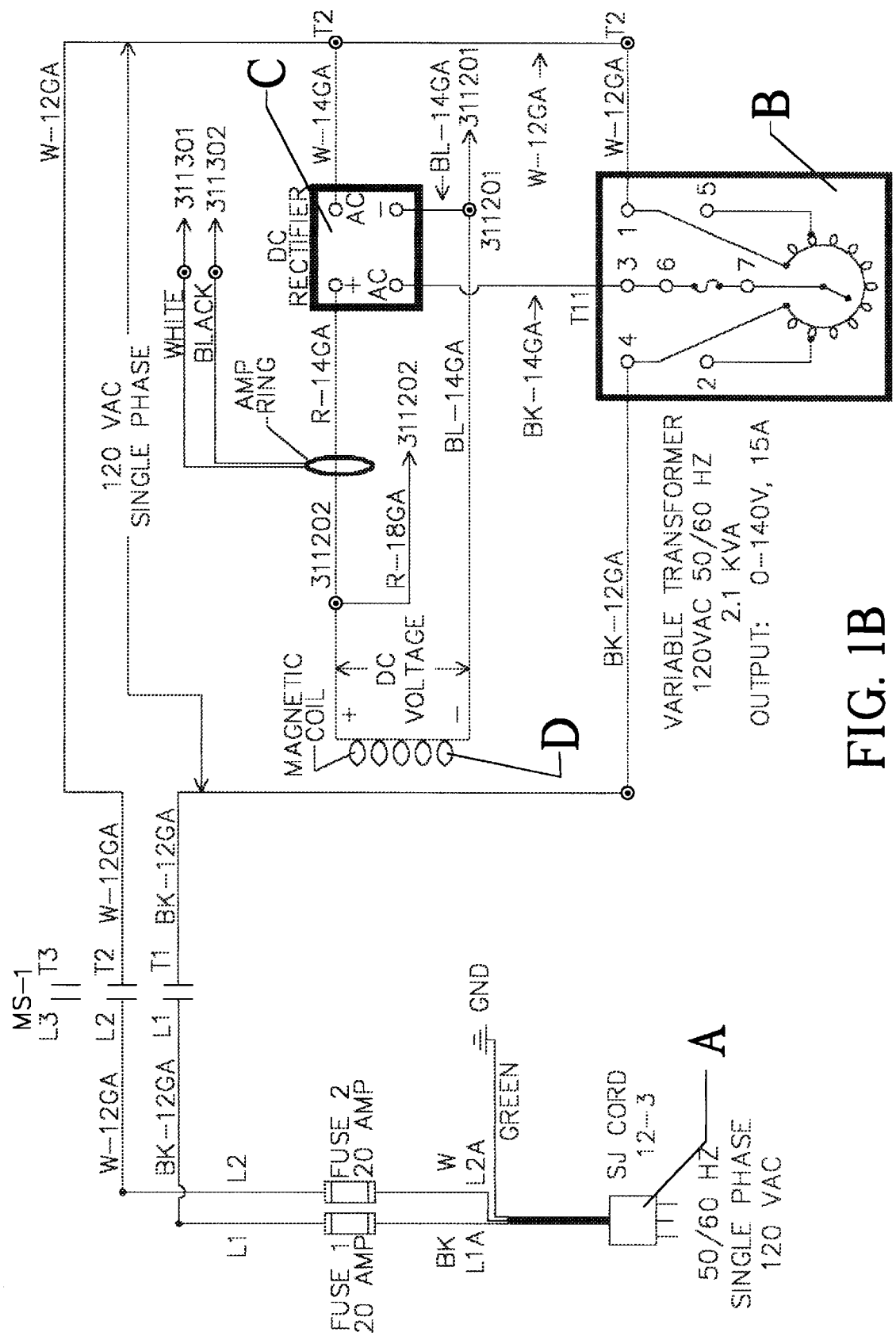

With reference to the schematic diagrams designated as FIGS. 1A and 1B, a source of electrical energy, preferably 110 or 220 volts in the United States, is designated generally by the reference letter A. An AC transformer, designated generally by the reference letter B and labeled "VOLTAGE REGULATOR", is electrically connected to the source A by a conventional power cord preferably rated to handle the input voltage of the source.

The transformer varies the AC input voltage. The AC output is then passed through a single or series of bridge rectifiers C (i.e., labeled as "BRIDGE RECTIFIER"). The bridge rectifier(s) preferably provide either a full wave or half wave rectification of the wave form to a 60 or 120 cycles per second DC "positive" (i.e., above the reference line on a sinusoidal oscilloscope) wave form. The fully rectified wave form from the bridge rectifier(s) is then passed to the free ends of the coil designated generally by the reference letter D and labeled "DEVICE" for convenience.

Figure 1C:
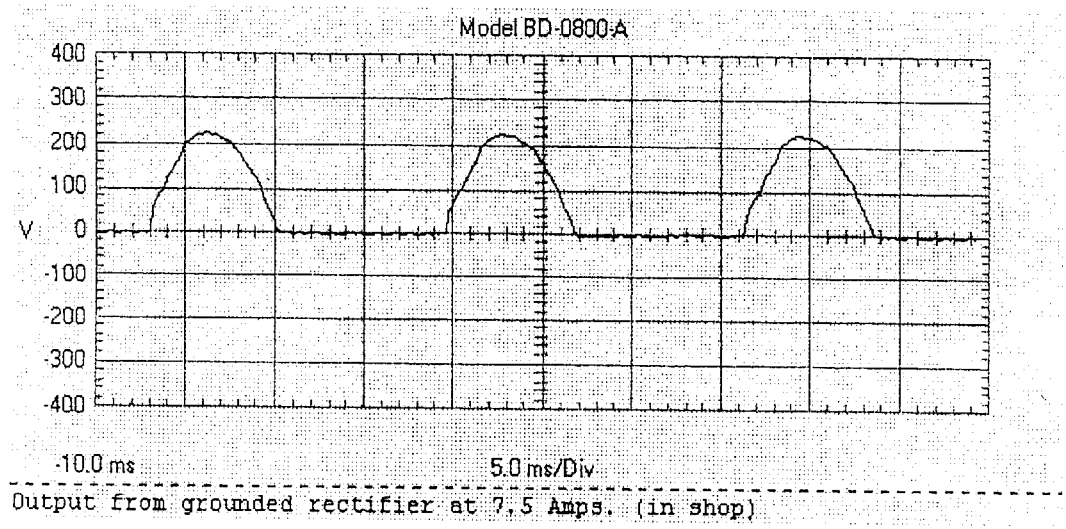
FIG. 1C is a graph illustrating the half rectified wave form produced by an embodiment of the present invention.
Figure 1D:
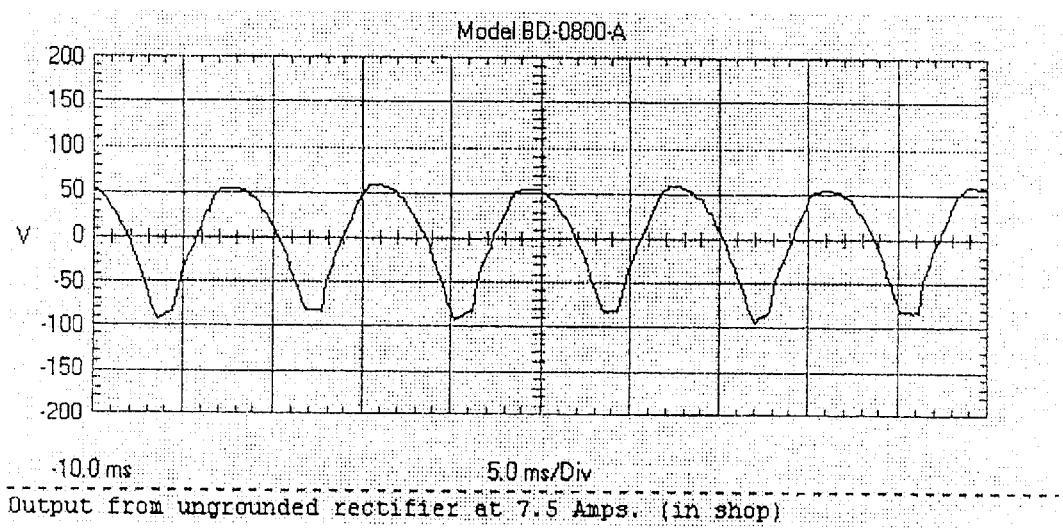
FIG. 1D is a graph illustrating the fully rectified wave form produced by an embodiment of the present invention.

FIGS. 1C and 1D are graphs illustrating the half rectified and fully rectified, respectively, wave form produced by an eight hundred (800) winding embodiment of the present invention. The sample graphs were taken when the field strength within the confines of the embodiment tested was set to produce 7.5 amps of current.

Figure 2:
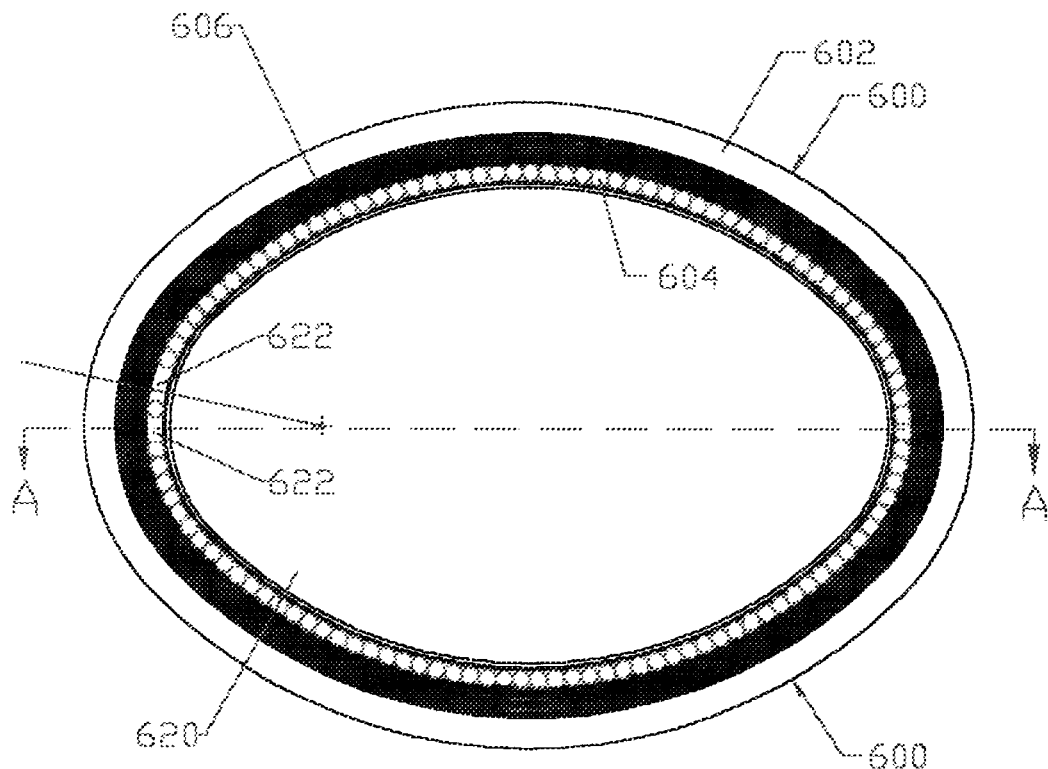
FIG. 2 is a side view of an embodiment of the present invention showing the relative orientation of the magnetic components and coil component and having a portion of the frame removed for clarity.
Figure 3:
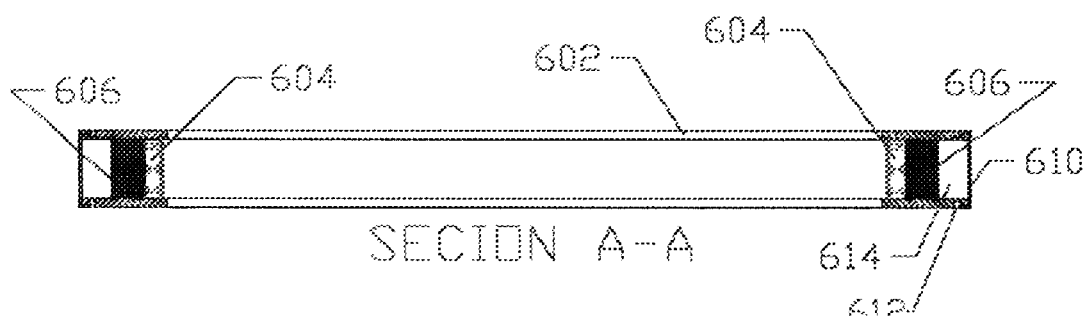
FIG. 3 is a cross-sectional view taken along line A—A of FIG. 2.

With reference to FIGS. 2 and 3, an embodiment of the device component of the present invention is designated generally by the reference number 600. A portion of the device frame 602 has been partially removed from FIG. 2 in order to show the permanent magnets 604 and the interiorly wrapped coil 606 in their preferred orientation. The coil winding 606 overlies the belt or annular layer of permanent magnets 604. A cover 610 is provided as a means of protecting and shielding the coil 606 during operation.

Within the coil assembly are a plurality of optional thermal sensors (not shown in FIGS. 2 and 3), of either resistance or thermocouple type which measure and indicate the coil temperature at various points.

Cover 610 can be a section of raceway cover which includes a cooperating tongue and groove snap connection 612 so that the cover may be removed to service the interior magnetic and/or coil components of the device. As such, the existence of the cover attached to the device frame 602 and the disposition of the magnet and/or coil establish an air space 614 (FIG. 3) between the frame 602, coil 606 and cover 610. The air space 614 provides a means of convective heat transfer such that if an air flow in the air space 614 were created, the flow of air would have a tendency to cool the coil 606 and magnets 604 when they become heated after the coil 606 in energized in the manner described below.

The orientation of the coil 606 and the magnets 604 is readily observed. Cross-section line A—A, which also serves as a vertical axis and horizontal line L, which serves as a horizontal axis, define the centroid of the interior channel 620 of the device. As shown in FIG. 2, there are a pair of gaps 622 in the annular layer or belt of magnets 604. The gaps are provided so as to establish an open circuit condition in case the magnets themselves which are typically made of some metal do become conductors by virtue of their close proximity to the coil.

Figure 4:
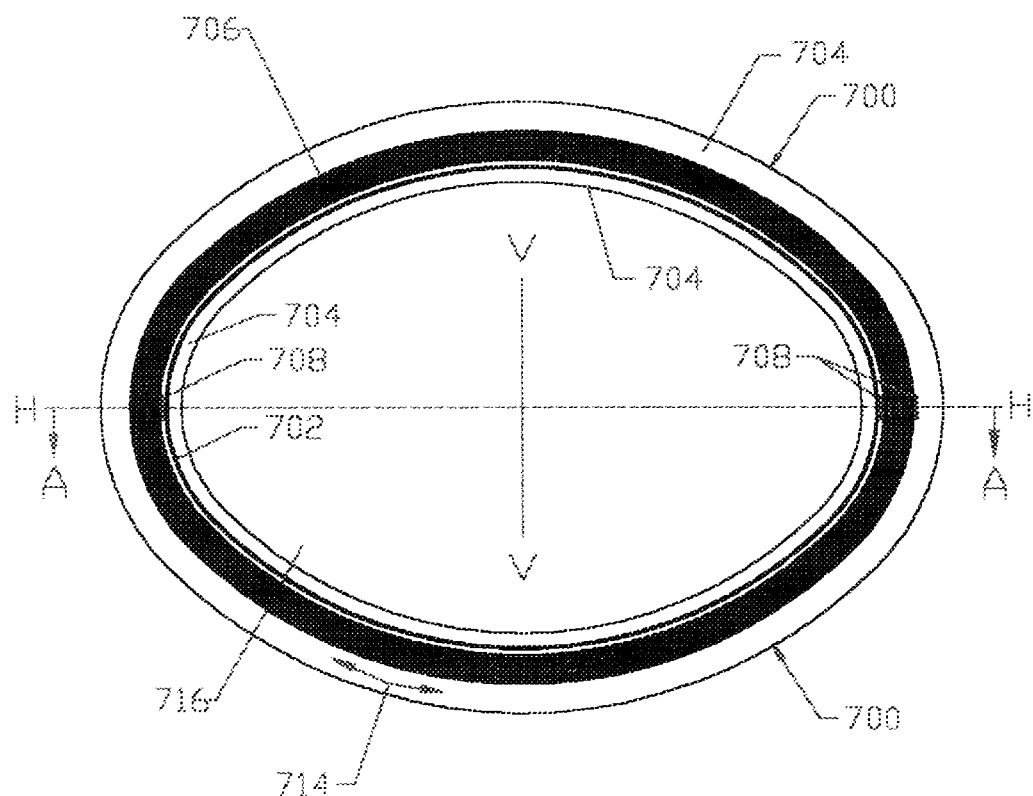
FIG. 4 is side view of the preferred embodiment of the present invention showing the relative orientation of the coil component and having a portion of the frame removed for clarity.
Figure 5:
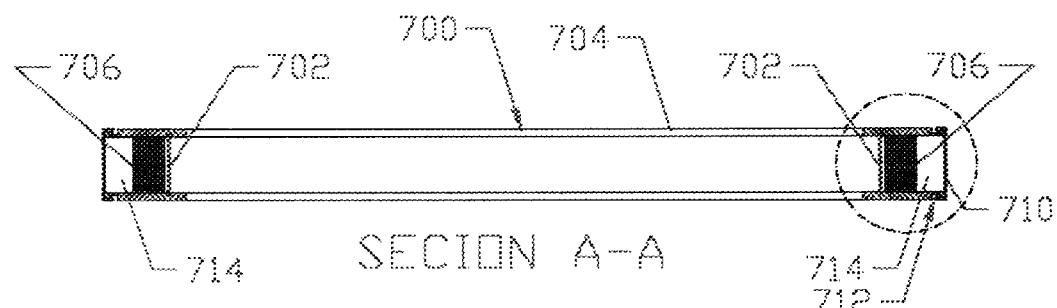
FIG. 5 is a cross-sectional view of the preferred embodiment taken along line A—A of FIG. 4.

With reference to FIGS. 4–5, the preferred embodiment of the coil assembly of the present invention is designated generally by the reference numeral 700. Embodiment 700 includes a frame component 702. The side plates 704 (see FIGS. 3–7) cover the coil 706 as it is wrapped around the frame 702. One of the side plates has been removed from FIG. 2 for visual clarity of the coil 706 but the side plates 704 are preferably rigidly attached to the frame 702 in a working embodiment of the invention.

Within the coil assembly 704 are a plurality of optional thermal sensors 708, of either the resistance or thermocouple type. The sensors are provided as a way of measuring the coil temperature at various points but do not affect the operation of the invention and its useful effect (i.e., angiogenesis and growth retardation of cancerous tumors).

A cover 710 is preferably rigidly secured to the frame. Attachment of the cover 710 to the frame 702 in the manner shown in the figures creates an air space 714 between the coil 706 and cover 710. The cover 710 may be snapped in place by a snap fit cooperation of the cover and the frame 712, or in the alternative the cover may be rigidly and securely attached by numerous others means of securement. The air space 714 allows for convective heat transfer from the coil 706 to the air within the air space 714. If an air flow is induced in the air space 714, the flow of air would have a tendency to cool the coil 706 if it heats up during use.

Figure 6:
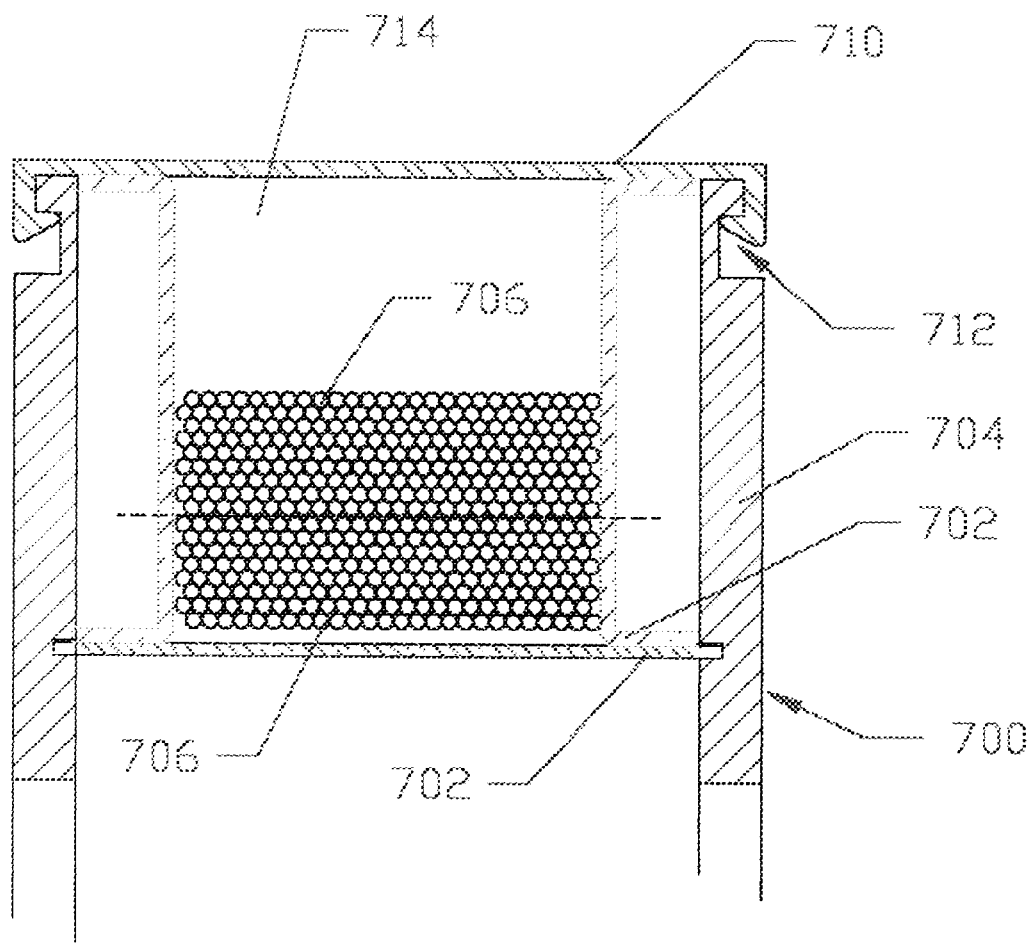
FIG. 6 is an enlarged sectional view of the portion of the preferred embodiment bounded by the viewing circle of FIG. 5 and further including a cover component.

With reference to FIGS. 5 and 6, the orientation of the frame 702, the side plates 704 and the coil 706, are readily observed. Cross-section line A—A of FIG. 4, which also serves as a vertical axis V intersects the horizontal axis H to define an approximate interior centroid of the interior 716 of the device (FIG. 4). When a current flow is induced into the coil 706, a magnetic field around the coil is established pursuant to the right hand rule. The magnetic lines of flux (not shown) are either to the left or to the right depending upon the frame of reference and the direction of current flow in the coil 706.

Figure 7:
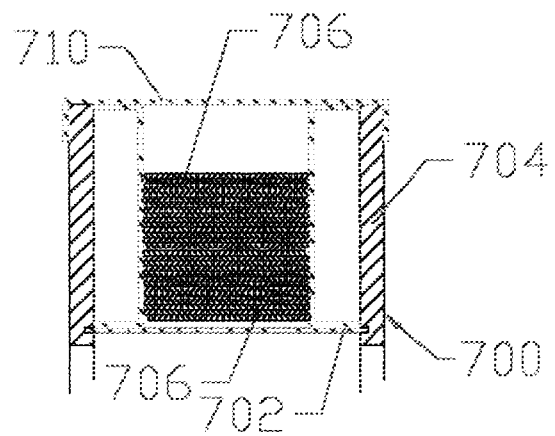
FIGS. 7–9 are alternate embodiments of the present invention shown in FIG. 6.
Figure 8:
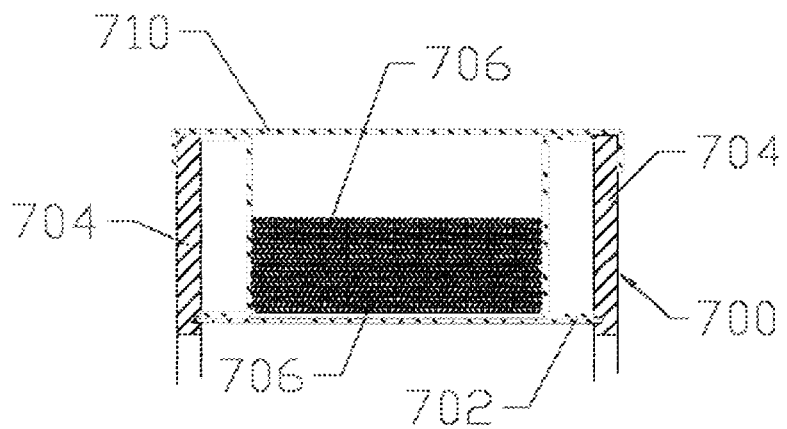
Figure 9:
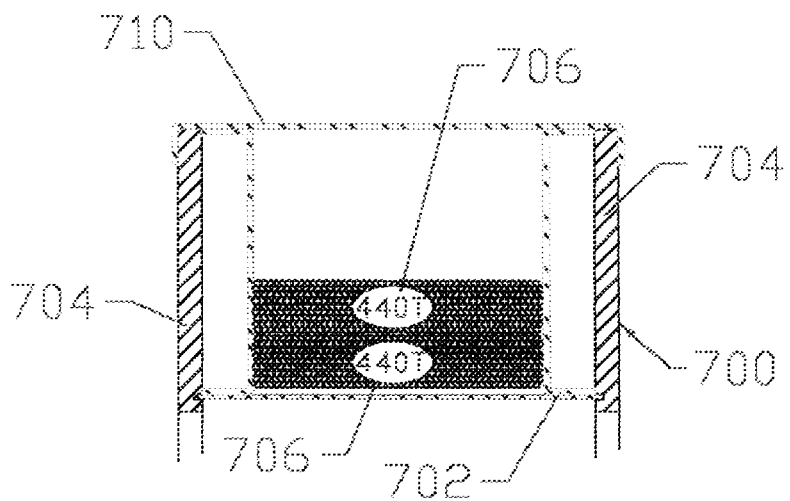

FIGS. 7–9 illustrate a variety of device profiles in order to demonstrate the various configurations the coil 706 may have depending upon the width of the frame. As shown in FIGS. 6 and 9, the device may also multiple coils 706 in a stacked or adjacent relationship as denoted by the hypothetical dashed dividing line of those figures. An optimum coil thickness with respect to width is believed to help establish a more uniform minimum heat generation within the coil 706.

DATA EXAMPLE

The following example provides actual data obtained from three (3) independent tests in human to determine if the inventive device and method are useful for relieving pain associated with degenerative diseases and disorders. The summary of the data and results is set forth below. The data illustrates a before and after pain rating for the various study participants. Some of the twenty nine (29) participants indicated having pain in more than one location of their body. Each participant completed the baseline (i.e., pretreatment) tests, treatment, and follow-up phases of the study. The magnetic field exposure data and pain relief data was systematically collected, tabulated and is set forth below in the tables. The apparatus and method of the present invention were found to be useful for relieving pain associated with degenerative diseases and disorders.

DATA TABLES

EXAMPLES

TABLE 1

Estimated Cumulative Magnetic Field Strength Exposure Over 4 to 6 Days

| CHIEF COMPLAINT CATEGORY | TOTAL # OF SUBJECTS | % Relief After Exp. | % Relief Evening After Exp. | % Relief Follow-up | % Relief 0% | % Relief <30% | % Relief >30% |
|---|---|---|---|---|---|---|---|
| Back | 7 | 6 | 6 | 4 | 0 | 3 | 4 |
| Leg | 8 | 5 | 5 | 5 | 0 | 2 | 6 |
| Knee | 3 | 3 | 3 | 3 | 0 | 1 | 2 |
| Neck and Shoulder | 3 | 3 | 3 | 3 | 0 | 1 | 2 |
| TMJ Disorder | 3 | 3 | 3 | 3 | 0 | 0 | 3 |
| Plantar Fascitis | 2 | 2 | 2 | 2 | 0 | 1 | 1 |
| Fibromyalgia Gp. 1 | 6 | 2 | 2 | 3 | 2 | 3 | 1 |
| Fibromyalgia Gp. 2 | 2 | 2 | 2 | 2 | 0 | 0 | 2 |

TABLE 2

Summary of the Results from % Pain Relief - Treatment and Follow-up Phases of the Study

| CHIEF COMPLAINT CATEGORY | Total # of Subjects | Exposures Per Day | Number of Days | Exposure Time (minutes) | Exposure Level (Gauss) | Cumulative Exposure (Gauss) |
|---|---|---|---|---|---|---|
| Back | 7 | 6 | 4 | 30 | 160 | 19,200 |
| Leg | 8 | 5 | 4 | 30 | 160 | 19,200 |
| Knee | 3 | 3 | 4 | 30 | 160 | 19,200 |
| Neck and Shoulder | 3 | 3 | 4 | 30 | 160 | 19,200 |
| TMJ Disorder | 3 | 3 | 4 | 30 | 160 | 19,200 |
| Plantar Fascitis | 2 | 2 | 4 | 30 | 160 | 19,200 |
| Fibromyalgia Gp. 1 | 6 | 2 | 6 | 30 | 110 | 19,800 |
| Fibromyalgia Gp. 2 | 2 | 2 | 6 | 30 | 160 | 28,800 |

What is claimed is:

1. A method of relieving temporomandibular joint pain comprising the steps of:
    providing a DC magnetic field generating device including a magnetic field component generated by a current carrying coil;
    energizing the current carrying coil enabling the DC magnetic field to be concentrated within a substantially planar area defined by a central passageway of a device frame; and
    placing a biological subject in the DC magnetic field and exposing the biological subject to said DC magnetic field.

2. The method of claim 1, wherein:
    the method of relieving pain associated with degenerative diseases and disorders is a method for relieving pain categorized within the pain group consisting of: myofacial pain, plantar fascitis, back, leg and neck pain.

3. The method of claim 1, further comprising the step of:
    providing a combined DC magnetic field generating device including a plurality of turns of wire and a plurality of permanent magnets.

4. The method of claim 3, further comprising the step of:
    applying an electrical voltage drop across the ends of the wire.

5. The method of claim 1, further comprising the step of:
    energizing the coil with an electrical current greater than 1 amp and less than 15 amps.

6. The method step of claim 5, wherein:
    the amperage range is from between 5 amps and 10 amps.

7. An apparatus for relieving pain associated with degenerative diseases and disorders in humans, comprising means for producing a magnetic field, wherein the means includes:
    a frame having a continuous sidewall and a central passageway extending therethrough,
    a coil made of electrically conducting material wrapped continuously around the frame and the central passageway; and
    a source of DC electrical energy operably connected to the coil for supplying DC electrical current to the coil and establishing a DC magnetic field concentrated within a substantially planar area defined by the central passageway and bounded by the frame.

8. The apparatus of claim 7, further comprising:
    a cover removably attached to the frame to shield the coil.

9. The apparatus of claim 7, further comprising:
    a switch capable of regulating the direction of the current flow through the wire.

10. The apparatus of claim 7, wherein:
    the apparatus for relieving pain associated with degenerative diseases and disorders is an apparatus for relieving pain associated with degenerative diseases and disorders within the pain group consisting of: myofacial pain, plantar fascitis, back, leg and neck pain.

11. The apparatus of claim 7, further including:
    a substantially elliptical frame.

12. The apparatus of claim 7, such that the coil, further comprises:
    a plurality of coils.

13. The apparatus of claim 12, such that the plurality of coils, further comprises:
    at least one coil having between 200 and 800 turns of wire.

14. A device for relieving myofacial pain, comprising:
    a frame having spaced apart side defining a central passageway and a substantially planar area thereof confined within the frame and bounded by an inside edges of each of the spaced apart sides;

coil means including a source of DC electrical energy operably connected to at least one coil of electrically conducting wire enabling a DC electrical current to be applied to the wire for establishing a DC magnetic field concentrated within the substantially planar area defined by the central passageway and bounded by the frame.

15. The device of claim 14, further comprising:

a substantially elliptical frame.

16. The device of claim 14, such that the coil of electrically conducting wire wrapped about the frame, further comprises:

a plurality of coils.

17. The device of claim 14, such that the coil, further comprises:

a coil having between 200 and 800 turns of wire.

18. The device of claim 16, such that the plurality of coils, further comprises:

at least one coil having between 200 and 800 turns of wire.

19. The device of claim 14, further comprising:

a plurality of magnets positioned adjacent the coil and held in place by the frame.

20. The device of claim 19, wherein:

The coil overlies the plurality of magnets.

* * * * *